United States Patent
Wu et al.

(10) Patent No.: US 10,267,738 B2
(45) Date of Patent: Apr. 23, 2019

(54) METHOD AND DEVICE FOR CHIRALITY ASSIGNMENT OF CARBON NANOTUBE

(71) Applicants: Tsinghua University, Beijing (CN); HON HAI PRECISION INDUSTRY CO., LTD., New Taipei (TW)

(72) Inventors: Wen-Yun Wu, Beijing (CN); Jing-Ying Yue, Beijing (CN); Xiao-Yang Lin, Beijing (CN); Qing-Yu Zhao, Beijing (CN); Kai-Li Jiang, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 404 days.

(21) Appl. No.: 14/838,385

(22) Filed: Aug. 28, 2015

(65) Prior Publication Data
US 2016/0061718 A1   Mar. 3, 2016

(30) Foreign Application Priority Data
Aug. 29, 2014 (CN) .......................... 2014 1 0434471

(51) Int. Cl.
*G01N 21/65* (2006.01)
*G01N 21/21* (2006.01)
(Continued)

(52) U.S. Cl.
CPC ............. *G01N 21/65* (2013.01); *B82B 3/009* (2013.01); *G01J 3/44* (2013.01); *G01N 21/21* (2013.01);
(Continued)

(58) Field of Classification Search
CPC ... G01J 3/44; G01N 2021/4792; G01N 21/21; G01N 21/6458; G01N 21/65;
(Continued)

(56) References Cited

U.S. PATENT DOCUMENTS 5,633,724 A * 5/1997 King .................... G01N 21/552
                                                         356/136
9,104,020 B2   8/2015 Knebel et al.
(Continued)

FOREIGN PATENT DOCUMENTS

CN        2739617 Y     11/2005
CN      103048272 A      4/2013
(Continued)

OTHER PUBLICATIONS

Daniel Y. Joh, Lihong H. Herman, Sang-Yong Ju, Jesse Kinder, Michael A. Segal, Jeffreys N. Johnson, Garnet K. L. Chan, and Jiwoong Park, "On-Chip Rayleigh Imaging and Spectroscopy of Carbon Nanotubes," Nano Letters 2011 11 (1), 1-7, DOI: 10.1021/nl1012568.*

(Continued)

*Primary Examiner* — Kara E. Geisel
*Assistant Examiner* — Violeta A Prieto
(74) *Attorney, Agent, or Firm* — ScienBiziP, P.C.

(57) ABSTRACT

A method for assigning chirality of carbon nanotube is provided. Firstly, carbon nanotube sample, an optical microscope with a liquid immersion objective and a liquid are provided. Secondly, the carbon nanotube sample is immersed in the liquid. Thirdly, the carbon nanotube sample is illuminated by an incident beam to generate resonance Rayleigh scattering. Fourthly, the liquid immersion objective is immersed into the liquid to get a resonance Rayleigh scattering (RRS) image of the carbon nanotube sample. Fifthly, spectra of the carbon nanotube sample are measured to obtain chirality of the carbon nanotube sample.

16 Claims, 13 Drawing Sheets

(51) Int. Cl.
*G01J 3/44* (2006.01)
*G01N 21/64* (2006.01)
*G01N 21/47* (2006.01)
*B82B 3/00* (2006.01)
*G02B 21/33* (2006.01)

(52) U.S. Cl.
CPC ......... *G01N 21/6458* (2013.01); *G02B 21/33* (2013.01); *G01N 2021/4792* (2013.01); *H01J 2201/30469* (2013.01)

(58) Field of Classification Search
CPC ............ G01N 21/658; H01J 2201/3046; H01J 9/025; B82B 3/009
See application file for complete search history.

(56) References Cited

U.S. PATENT DOCUMENTS

| | | | | |
|---|---|---|---|---|
| 2005/0225766 | A1* | 10/2005 | Hansen | G01N 15/1459 356/436 |
| 2010/0285656 | A1* | 11/2010 | Esconjauregui | B01J 23/74 438/478 |
| 2011/0297556 | A1* | 12/2011 | Unwin | G01N 27/308 205/792 |
| 2012/0193785 | A1* | 8/2012 | Lin | H01L 21/76229 257/737 |
| 2013/0107358 | A1* | 5/2013 | Knebel | G02B 21/0032 359/385 |
| 2015/0140211 | A1* | 5/2015 | Strobl | C23C 16/26 427/249.6 |
| 2016/0061664 | A1* | 3/2016 | Wu | G01J 3/4412 356/301 |
| 2016/0061733 | A1* | 3/2016 | Wu | G01N 21/65 356/301 |
| 2016/0061734 | A1* | 3/2016 | Wu | G01N 21/65 356/301 |
| 2016/0284811 | A1* | 9/2016 | Yu | H01L 29/454 |

FOREIGN PATENT DOCUMENTS

| | | |
|---|---|---|
| CN | 103091825 A | 5/2013 |
| TW | 201430330 A | 8/2014 |

OTHER PUBLICATIONS

Ado Jorio, Gene Dresselhaus, Mildred S. Dresselhaus, "Carbon Nanotubes", 2001, Springer, ISBN 978-3-540-72864-1, DOI 10.1071/978-3-540-72865-8.*

Yung Joon Jung, Bingqing Wei,Robert Vajtai, and, Pulickel M. Ajayan, Yoshikazu Homma,Kuniyil Prabhakaran, and, and Toshio Ogino, "Mechanism of Selective Growth of Carbon Nanotubes on SiO2/Si Patterns," Nano Letters 2003 3 (4), 561-564; DOI: 10.1021/nl034075n.*

Daniel Y. Joh et al."On-chip Rayleigh imaging and spectroscopy of carbon nanotubes." Nano Lett. Jan. 12, 2011;11(1)1-72010-08-02 doi: 10.1021/nl1012568. Epub Aug. 2, 2010.

Jiangtao Wang et al. "Vapor-Condensation-Assisted Optical Microscopy for Ultralong Carbon Nanotubes and Other Nanostructures", Nano Letters, May 22, 2014,dx.doi.org/10.1021/nl5016969/Nano Lett. 2014,14,3527-3533.

Matthew Y. Sfeir et al. "Probing Electronic Transitions in Individual Carbon Nanotubes by Rayleigh Scattering", Science, vol. 306, p. 1540-1543,2004/10/28 DOI: 10.1126/science.1103294.

* cited by examiner

METHOD AND DEVICE FOR CHIRALITY ASSIGNMENT OF CARBON NANOTUBE

RELATED APPLICATIONS

This application claims priority to Chinese Patent Application No. 201410434385.2 filed on Aug. 29, 2014 in the China Intellectual Property Office, the contents of which are incorporated by reference herein.

FIELD

The subject matter herein generally relates to method and device for assigning chirality of carbon nanotubes, and more particularly to a method and device for assigning chirality of carbon nanotubes by spectral measurement method.

BACKGROUND

Carbon nanotubes obtained by conventional methods, is usually a mixture of carbon nanotubes with different chiralities, and different lengths. The carbon nanotubes with different chiralities have different properties, such as thermal, electrical, optical and mechanical properties. Therefore, the chirality assignments of the carbon nanotubes has great significance for the application of carbon nanotubes.

A carbon nanotube is an ideal one dimensional material which has van-Hove singularities in electron density of states and has high optical sensitivity. Therefore, the chirality of a carbon nanotube can be assigned by various optical phenomena, such as resonance Rayleigh scattering (RRS). In 2001, using a tungsten lamp as white light source, Yu and Brus measured the Rayleigh scattering spectra of single-walled carbon nanotube (SWCNT) bundles, which reveal resonance peaks due to the optically allowed interband transitions in SWNTs. Three years later, supercontinuum (SC) white laser was applied to illuminate individual SWCNTs, which generated more distinct resonance Rayleigh scattering peaks. Though excitonic in nature, the resonance peaks are related to the van Hove singularities (vHs) in the electron density of states, thus enabling chirality assignment of SWCNTs. These resonance Rayleigh scattering peaks in visible region imply that the SWCNTs should appear colored. Considering the fact that vHs are widely spread in the electron density of states of 1-D nanomaterials, the nanoworld illuminated by white light should also be colorful. The displayed color information directly reflects the structures and physical properties of nanomaterials.

Because scattering cross-section of the of 1-D nanomaterials is very small weak, they are usually invisible under optical microscope, so as difficult to observe and collect. The chiralities of carbon nanotubes are not easily and effectively assigned in prior art.

Therefore the chirality assignment of nanomaterials, especially of CNTs by RRS is highly desirable and has long been attempted.

BRIEF DESCRIPTION OF THE DRAWINGS

Many aspects of the method and device for assigning chiralities of carbon nanotubes can be better understood with references to the following drawings. The components in the drawings are not necessarily drawn to scale, the emphasis instead being placed upon clearly illustrating the principles of the present optical microscopy system.

Figure 1:
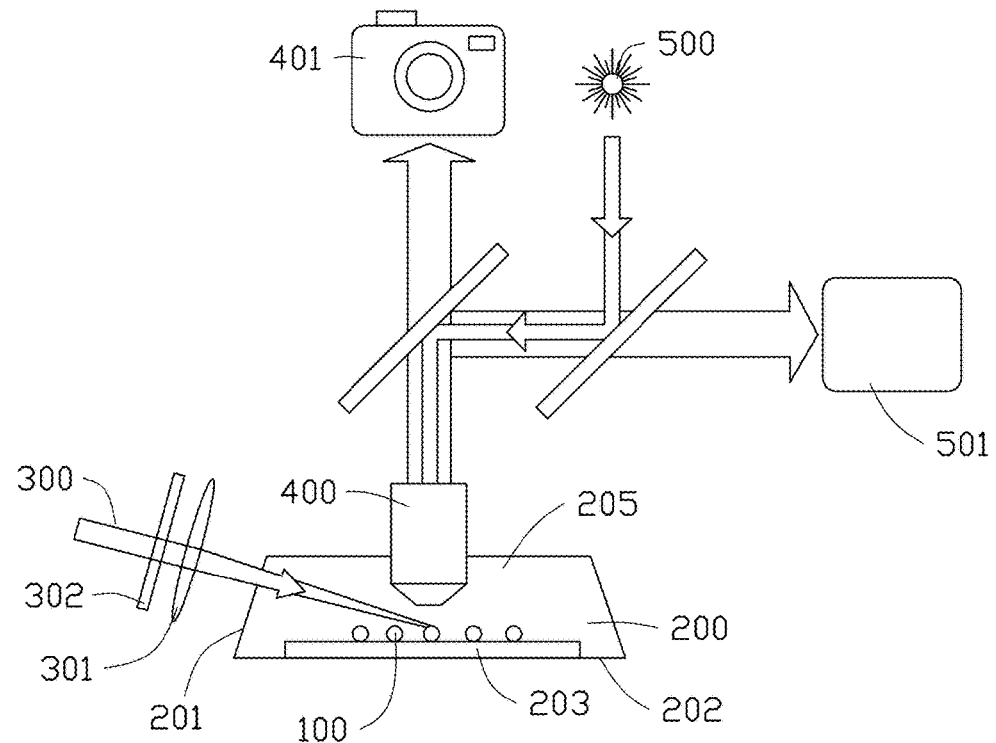
FIG. 1 is a schematic view of a measurement device system for imaging carbon nanotubes under optical microscopy and spectra collecting according to one embodiment.

Corresponding reference characters indicate corresponding parts throughout the several views. The exemplifications set out herein illustrate at least one present embodiment of optical microscopy system and method for using the same, in at least one form, and such exemplifications are not to be construed as limiting the scope of the disclosure in any manner.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasable connected. The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one.

References will now be made to the drawings to describe, in detail, various embodiments of the present epitaxial structures and methods for making the same.

Referring to FIG. 1, a method for assigning chiralities of carbon nanotubes is provided according to one embodiment. The method comprises steps of:

S1, providing carbon nanotube sample 100, an optical microscope with a liquid immersion objective 400 and a liquid 205;

S2, immersing the carbon nanotube sample 100 in the liquid 205;

S3, illuminating the carbon nanotube sample 100 by a incident beam 300 to generate resonance Rayleigh scattering;

S4, immersing the liquid immersion objective 400 into the liquid 205 to get a resonance Rayleigh scattering (RRS) image of the carbon nanotube sample 100; and S5, measuring spectra of the carbon nanotube sample 100 to obtain chirality of the carbon nanotube sample 100.

In step S1, the carbon nanotube sample 100 can be a plurality of carbon nanotubes 100 parallel with each other aligned on a substrate 203. In one embodiment, the plurality of carbon nanotubes 100 are single-walled carbon nanotubes horizontally aligned on the substrate 203 and parallel with each other. The substrate 203 can be a Si substrate coated with a $SiO_2$ layer. The substrate 203 has a thickness of about 500 nanometers. The $SiO_2$ layer has a thickness in a range from about 30 nanometers to about 300 nanometers. In one embodiment, the single walled carbon nanotubes are obtained by chemical vapor deposition, and then transferred to Si substrate coated with 100 nm $SiO_2$ layer using polymethylmethacrylate (PMMA). When the $SiO_2$ layer has 100 nm thicknesses, the RRS image of the carbon nanotube sample 100 has good performance.

In step S1, the liquid 205 can be pure water or oil. The liquid immersion objective 400 can be water immersion objective or oil immersion objective according to the selection of the liquid 205. In one embodiment, the liquid 205 is water, and the liquid immersion objective 400 is water immersion objective.

In step S2, the carbon nanotube sample 100 and the substrate 203 are completely immersed in the liquid 205, so as to decrease scattering of the incident beam 300 near the substrate 203. Compared to the refractive index of air (1.0003), the refractive index of the liquid 205 (water 1.33) is closer to the refractive index of the substrate 203 (quartz 1.49), the closer refractive index of two mediums (water and quartz) can reduce the scattering of the incident beam 300 near the substrate 203. Furthermore, an "interface dipole enhancement effect" existed at the interface between the carbon nanotube sample 100 and the liquid 205 can enhance the resonance Rayleigh scattering of the carbon nanotube sample 100.

In step S2, to reduce substrate scattering, the liquid 205 can be hold in a container 200. The container 200 comprises a side surface 201 and a bottom surface 202. The side surface 201 is a planar quartz window. The substrate 203 is located on the bottom surface 202 and immersed in the liquid 205 contained in the container 200. An angle between the side surface 201 and the bottom surface 202 can be in a range from about 45 degrees to about 90 degrees. In one embodiment, the angle is 75 degrees.

In step S3, the incident beam 300 can be a white light with a continuous spectrum. The incident light 300 can be directly illuminated to the carbon nanotube sample 100, or coupled to illuminate to the carbon nanotube sample 100 by other means. Resonance Rayleigh scattering happens when the carbon nanotube sample 100 is illuminated by the incident beam 300. In one embodiment, a supercontinuum (SC) white laser (Fianium SC400) is used to provide the incident beam 300. The incident beam 300 is set vertical to the side surface 201 and illuminates to the carbon nanotube sample 100 through the side surface 201. Vertical setting of the incident beam 300 to the side surface 201 can effectively reduce dispersion and attenuation of the incident beam 300 at interface.

In one embodiment, the incident beam 300 can be filtered and focused before reach to the carbon nanotube sample 100. A filter 302 is used to filter out infrared light of the incident beam 300 so as to avoid heating effect which would cause the carbon nanotube sample 100 temperature rising. Thus, the carbon nanotube sample 100 can be protected. A focusing lens 301 can be used to increase intensity of the incident beam 300 to increase the effect of observation results.

In step S4, the liquid immersion objective 400 is used to collect resonance Rayleigh scattering light of the carbon nanotube sample 100. The carbon nanotube sample 100 can be real-time observed by the liquid immersion objective 400. The color, position and shape information of the carbon nanotube sample 100 can be collected by the optical microscope through the liquid immersion objective 400. In one embodiment, a camera 401 is connected to the optical microscope to record the RRS image of the carbon nanotube sample 100.

During resonance Rayleigh scattering of the carbon nanotube sample 100 happens, the color of the carbon nanotube sample 100 is associated with the chirality of the carbon nanotube sample 100. The carbon nanotubes having different chiralities have different colors when resonance Rayleigh scattering happened. Therefore, the RRS image of the carbon nanotube sample 100 can be used to determine: if the chiralities of at least two carbon nanotubes 100 are consistent, and the chirality at both sides of intramolecular junction of individual carbon nanotube of the carbon nanotube sample 100 whether changed.

Figure 2:
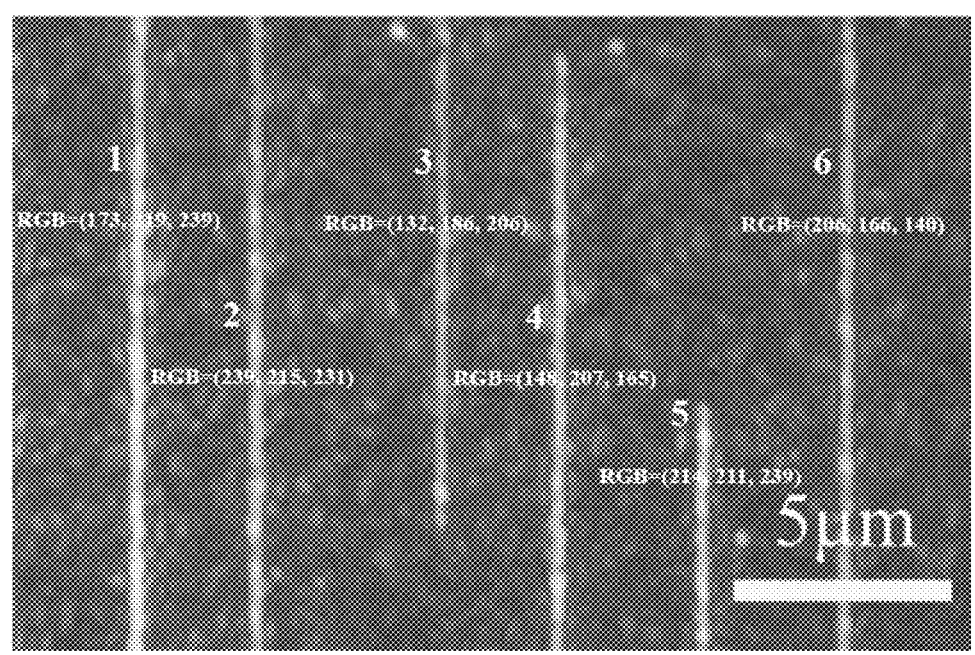
FIG. 2 is an RRS image of single-walled carbon nanotubes immersed in water according to one embodiment.
Figure 3:
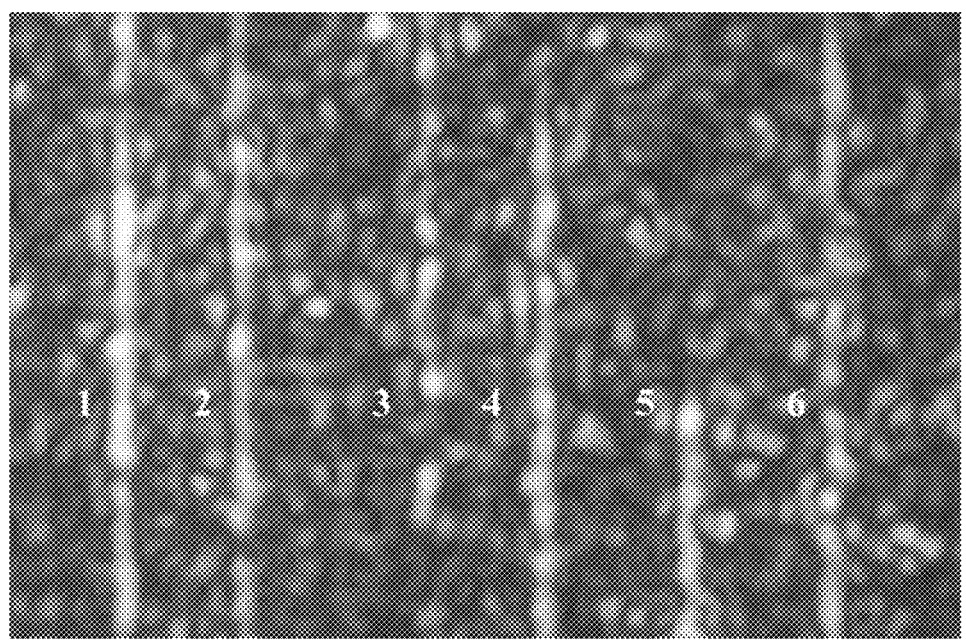
FIG. 3 is a RRS image of the same single-walled carbon nanotubes of FIG. 2 in air according to one embodiment.
Figure 4:
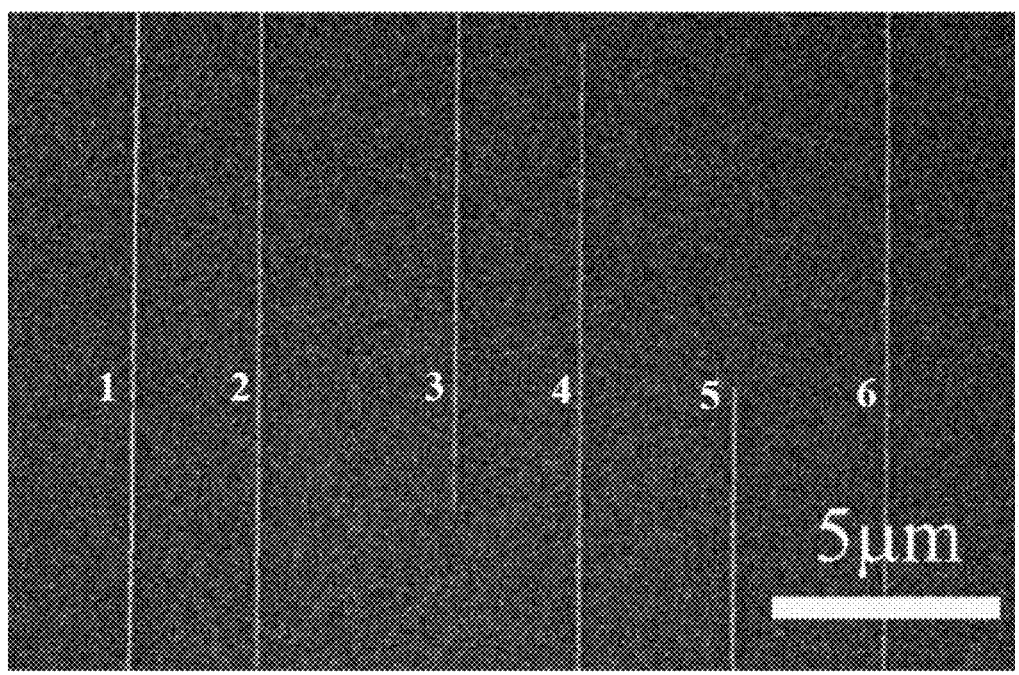
FIG. 4 shows a Scanning Electron Microscope (SEM) image of the single-walled carbon nanotubes in FIG. 2 and FIG. 3.

FIG. 2 and FIG. 3 are RRS images recorded by the camera 401 to same single-walled carbon nanotubes according to one embodiment. FIG. 2 is RRS image to the single-walled carbon nanotubes immersed in water according to one embodiment. The liquid immersion objective 400 is water immersion objective with magnification of 63×, and numerical aperture of 0.9. FIG. 3 is RRS image to the same single-walled carbon nanotubes in air observed by a general objective with magnification of 50×, and numerical aperture of 0.55. FIG. 4 shows a SEM image to the single-walled carbon nanotubes same with the FIG. 2-3.

There are six single-walled carbon nanotubes in FIG. 2, orderly numbered from 1 to 6. The color and RGB values according to each of the six single-walled carbon nanotubes are: light blue (173, 219, 219), pink (239, 215, 215), blue (132, 186, 186), green (148, 207, 207), purple (214, 211, 211), orange (206, 166, 166). The different colors of the six single-walled carbon nanotubes are corresponding to different chiralities of the six single-walled carbon nanotubes. FIG. 3 is the RRS image to the same single-walled carbon nanotubes of FIG. 2 in air. FIG. 2 is much better than FIG. 3.

Figure 5:
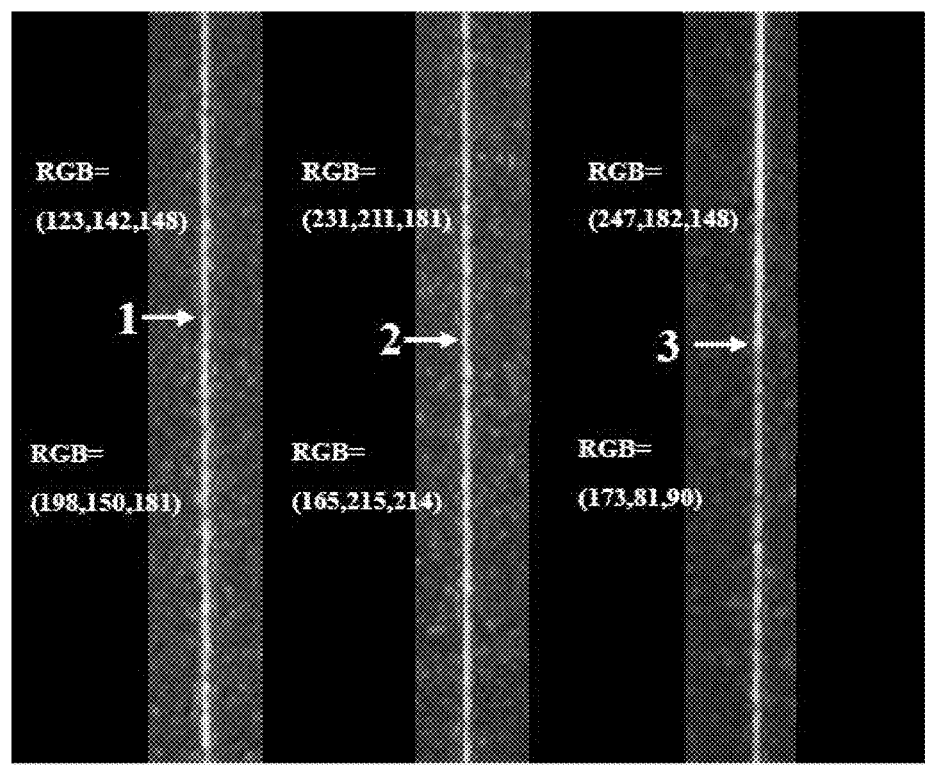
FIG. 5 is a RRS image of single-walled carbon nanotubes having intramolecular junction.

Referring to FIG. 5, a RRS image of single-walled carbon nanotubes having intramolecular junction is shown. The intramolecular junction is indicated by the arrow in FIG. 5. There are three single-walled carbon nanotubes orderly numbered from 1 to 3 in FIG. 5. The colors of each of the three single-walled carbon nanotubes at opposite sides of the intramolecular junction are different. A RGB value of the upper side of the intramolecular junction of the first single-walled carbon nanotube is (123, 142, 148). A RGB value of the lower side of the inramolecular junction of the first single-walled carbon nanotube is (198, 150, 181). A RGB value of the upper side of the intramolecular junction of the second single-walled carbon nanotube is (231, 211, 181). A RGB value of the lower side of the inramolecular junction of the second single-walled carbon nanotube is (165, 215, 214). A RGB value of the upper side of the intramolecular junction of the third single-walled carbon nanotube is (247, 182, 148). A RGB value of the lower side of the inramolecular junction of the second single-walled carbon nanotube is (173, 81, 90). Different colors at the upper side and the lower side of the intramolecular junction of the single-walled carbon nanotubes demonstrate the chirality at the intramolecular junction of the single-walled carbon nanotubes is changed.

Figure 6:
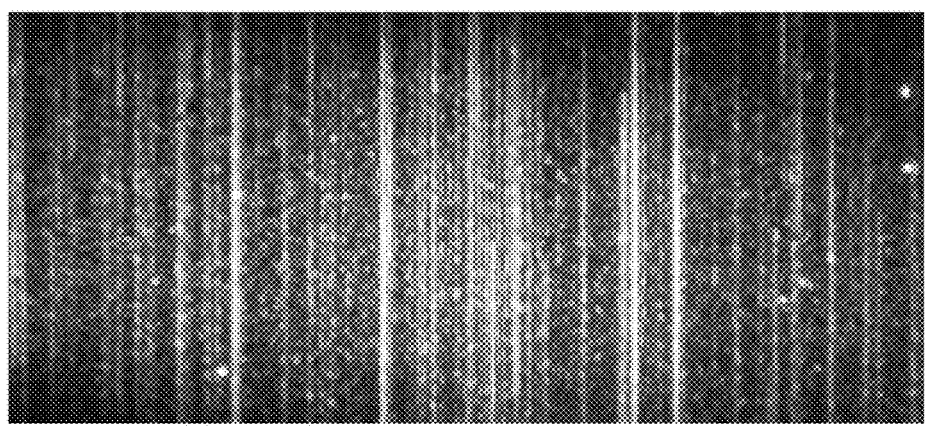
FIG. 6 is a RRS image of graphene strips according to one embodiment.

FIG. 6 is a RRS image of graphene strips according to one embodiment. The method in this description can also apply to the graphene strips.

In addition to color information, FIGS. 2, 3, 5 and 6 further comprises the position and shape information of the carbon nanotube sample 100. The position information can be used to locate the carbon nanotube sample 100.

In step S4, a resonance Rayleigh scattering light of the carbon nanotube sample 100 is collected by the optical microscope through the liquid immersion objective 400. A camera 401 can be used to record the color, position and shape information of the carbon nanotube sample 100. The camera 401 is connected to the optical microscope.

The color of the carbon naotube sample 100 in the event of resonance Rayleigh scattering is associated with the chirality of the carbon naotube sample 100. Carbon nanotubes with different chiralities exhibit different colors. Therefore, resonance Rayleigh scattering of the carbon nanotube sample 100 can be used to measure chirality assignment of the carbon nanotube sample 100 when the carbon nanotube sample 100 comprising a plurality of carbon nanotubes.

The method provided in this description can obtain the color, position, shape, length and density information of the carbon nanotube sample 100. A force can be applied to the carbon nanotube sample 100 during the observation, and the changes in the structural properties of the carbon nanotube sample 100 can be real-time observed under the optical microscope in the above process.

In step S5, the resonance Rayleigh scattering light of the carbon nanotube sample 100 through the liquid immersion objective 400 is finally transmitted into a spectrometer 501 to obtain spectral information of the carbon nanotube sample 100. The spectral information may be Rayleigh scattering spectra, Raman scattering spectra, or fluorescence spectral information. The spectral information can be used to further deduce chirality and the related physical properties of the carbon nanotube sample 100.

Figure 7:
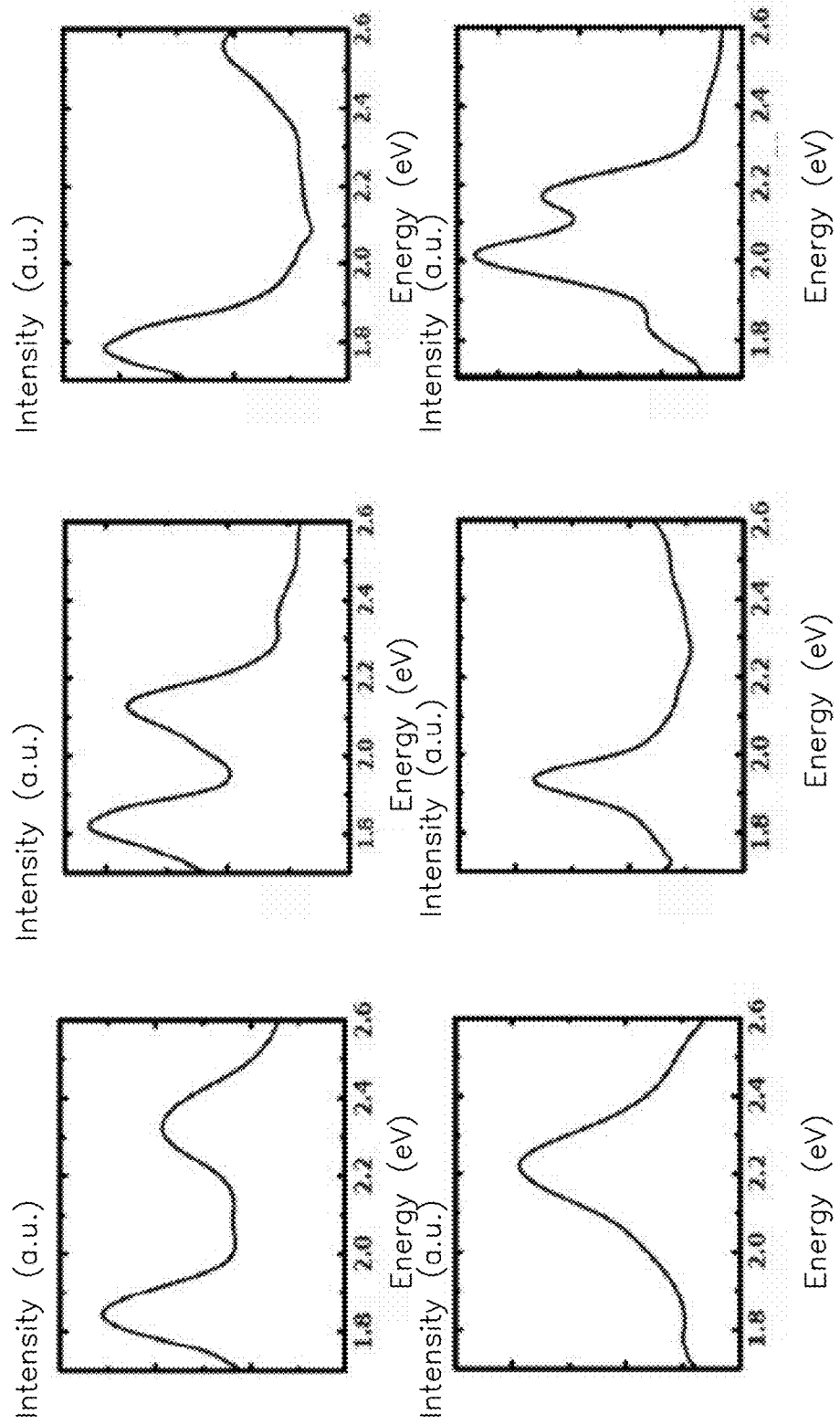
FIG. 7 is Rayleigh spectra of the single-walled carbon nanotubes in FIG. 2.

In one embodiment, the Rayleigh scattering spectra and the Raman scattering spectra of the carbon nanotube sample 100 are measured to obtain chiral index of the carbon nanotube sample 100. FIG. 7 is the resonance Rayleigh scattering spectra of the six single-walled carbon nanotubes (SWCNTs) in FIG. 2. The first, second, and sixth SWCNTs all have two resonant peaks in the visible region and the chiral indices are easily assigned. For the rest three SWCNTs with a single resonant peak in the visible region, additional diameter information provided by radial breathing mode (RBM) in Raman spectra of the rest three SWCNTs can greatly speed up the chirality assignment of the rest three SWCNTs. The Raman spectrum of the carbon nanotube sample 100 is excited by a light source 500. In one embodiment, the Raman spectra of the carbon nanotube sample 100 is obtained by steps of:

S51, measuring resonance Rayleigh scattering spectra of the carbon nanotube sample 100;

S52, selecting excitation wavelength needed to produce Raman scattering; and

S53, obtaining the Raman scattering of the carbon nanotube sample 100.

Traditionally it is time consuming to find out the excitation wavelength since resonant excitation is needed for RBM, but now with the help of the resonance information given by Rayleigh spectra, the excitation wavelength could be easily selected. For example, the third and fifth SWCNTs should be excited by a 633 nm laser and the forth by 514 nm.

Figure 8:
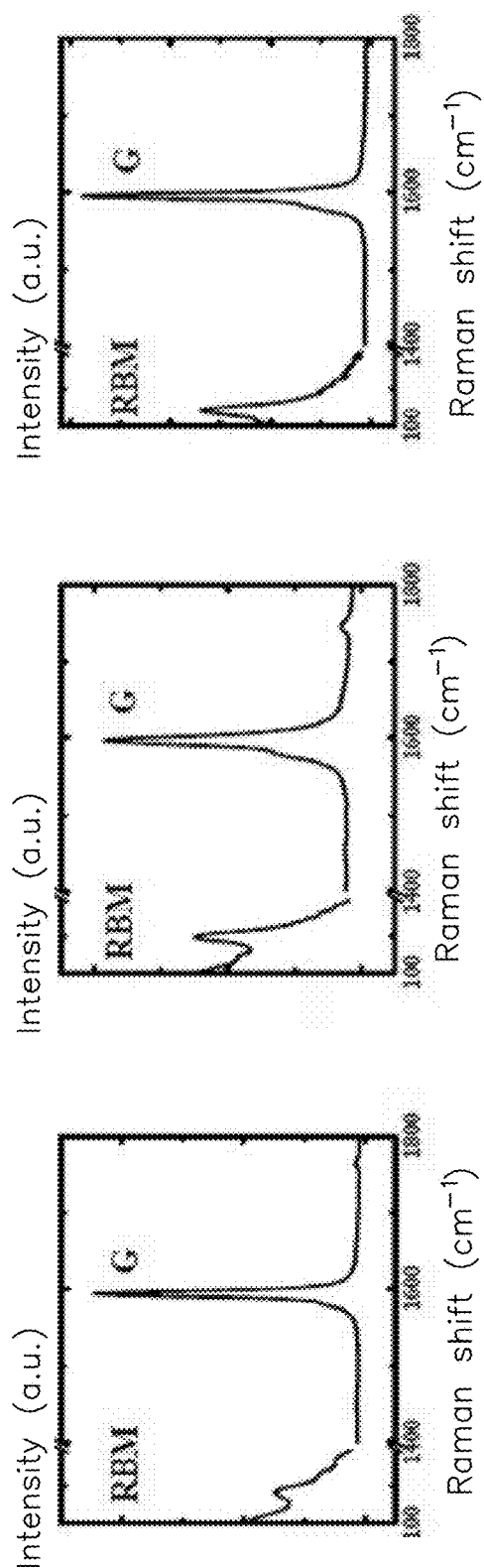
FIG. 8 is Raman spectra of the three single-walled carbon nanotubes (in FIGS. 3, 4 and 5).

Referring to FIG. 8, FIG. 8 is the Raman spectra of the third, forth and fifth SWCNTs. Combining Rayleigh and Raman spectra, the chiral indices of the six individual SWCNTs in FIG. 2 are assigned to be (35, 10), (17, 12), (22, 3), (13, 9), (19, 14), and (26, 21), respectively.

Figure 9:
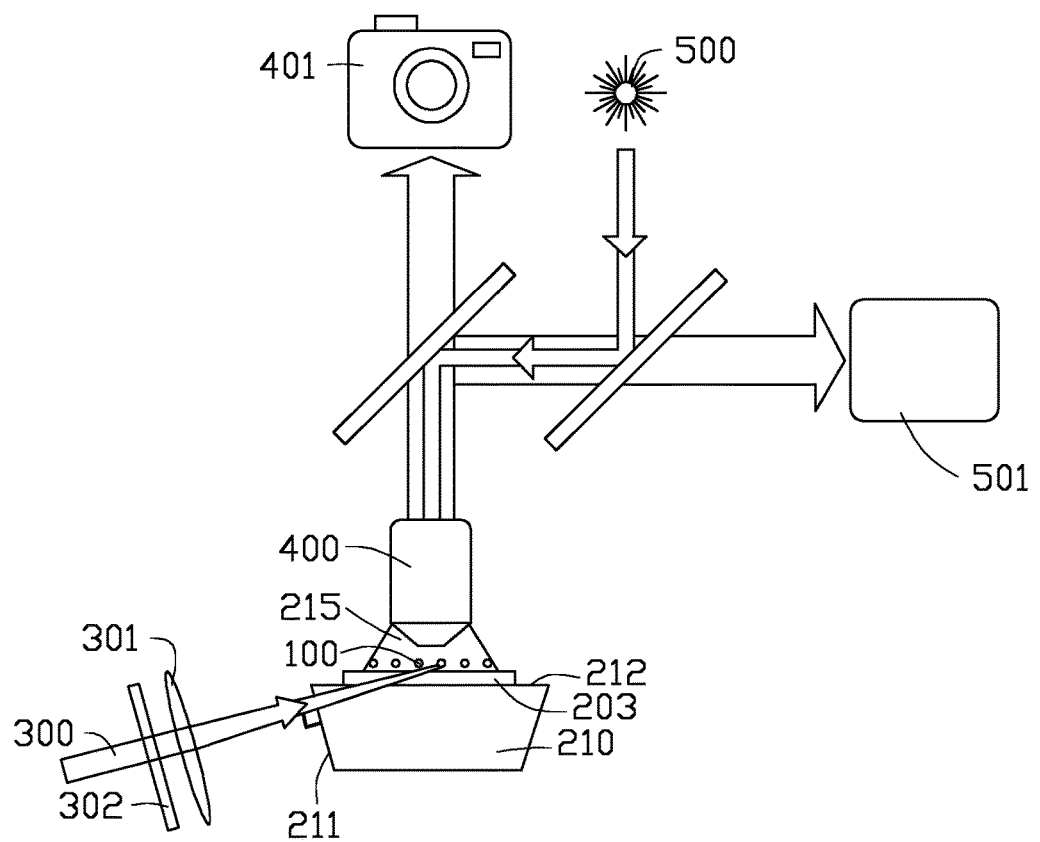
FIG. 9 is a schematic view of a measurement device system for assigning carbon nanotubes under optical microscopy and spectra collecting according to one embodiment.
Figure 10:
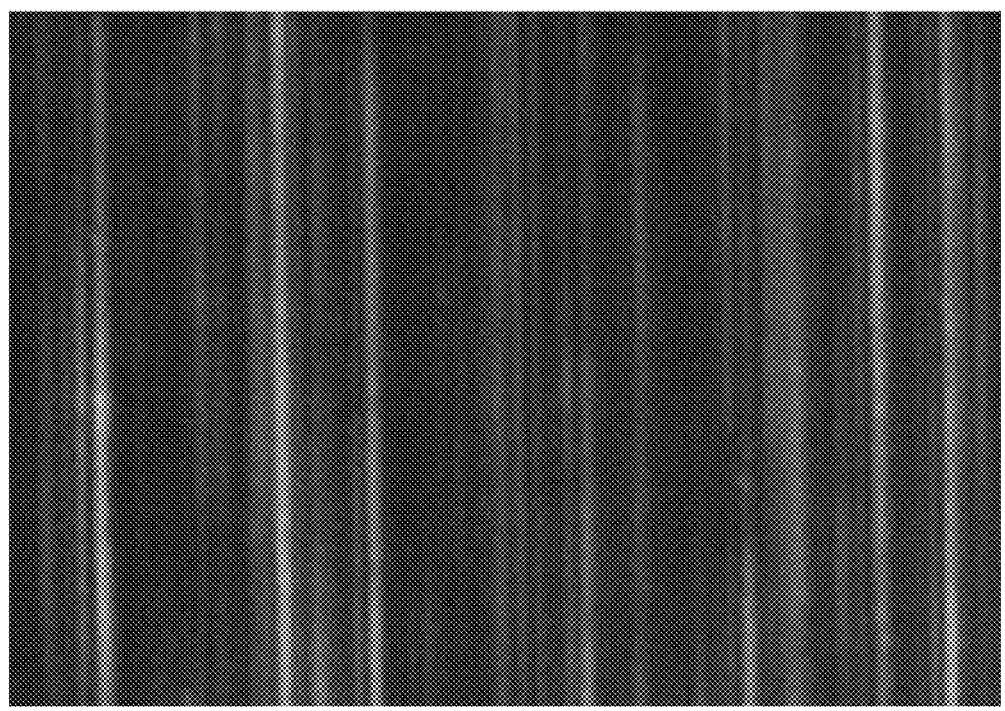
FIG. 10 is an RRS image of single-walled carbon nanotubes according to one embodiment.

Referring to FIG. 9, a method for assigning chiralities of carbon nanotubes is provided according to one embodiment. The method comprises steps of:

S10, providing a carbon nanotube sample 100, an optical microscope with a liquid immersion objective 400, a liquid 205 and a prism 210, wherein the prism 210 comprises a side surface 211 and a top surface 212, an angle between the side surface 211 and the top surface 212 is less than 90 degrees, and the carbon nanotube sample 100 is located on the upper surface 212;

S20, immersing the carbon nanotube sample 100 in the liquid 205;

S30, illuminating the carbon nanotube sample 100 by an incident beam 300 through the side surface 211 to generate resonance Rayleigh scattering;

S40, immersing the liquid immersion objective 400 into the liquid 205 to get a resonance Rayleigh scattering (RRS) image of the carbon nanotube sample 100; and S50, measuring resonance Rayleigh scattering spectra of the carbon nanotube sample 100 to obtain chirality of the carbon nanotube sample 100.

In step S20, the prism 210 is used to couple the incident beam 300, and can made of glass, quartz, or transparent plastic. An angle β defined between the side surface 211 and the top surface 212 is in a range from about 45 degrees to about 90 degrees. In one embodiment, the prism 210 is made of quartz, and the angle β is 75 degrees.

The carbon nanotube sample 100 can be directly located on the top surface 212. The carbon nanotube sample 100 can also be located on a substrate 203 first and then the substrate 203 is located on the surface 212. The substrate 203 is made of same material as the prism 210. In one embodiment, the substrate 203 is made of quartz.

In step S30, the incident beam 300 is set vertical to the side surface 211 and illuminate to the carbon nanotube sample 100 through the side surface 211. Vertical setting of the incident beam 300 to the side surface 211 can effectively reduce dispersion and attenuation of the incident beam 300 at interface.

A filter 302 can be used to filter out infrared light of the incident beam 300 so as to avoid heating effect which would cause the carbon nanotube sample 100 temperature rising. A focusing lens 301 can be used to increase intensity of the incident beam 300 to increase the effect of observation results.

In one embodiment, the liquid 205 is glycerine, the liquid immersion objective 400 is oil immersion objective with magnification of 100×, and numerical aperture of 1.30.

Figure 11:
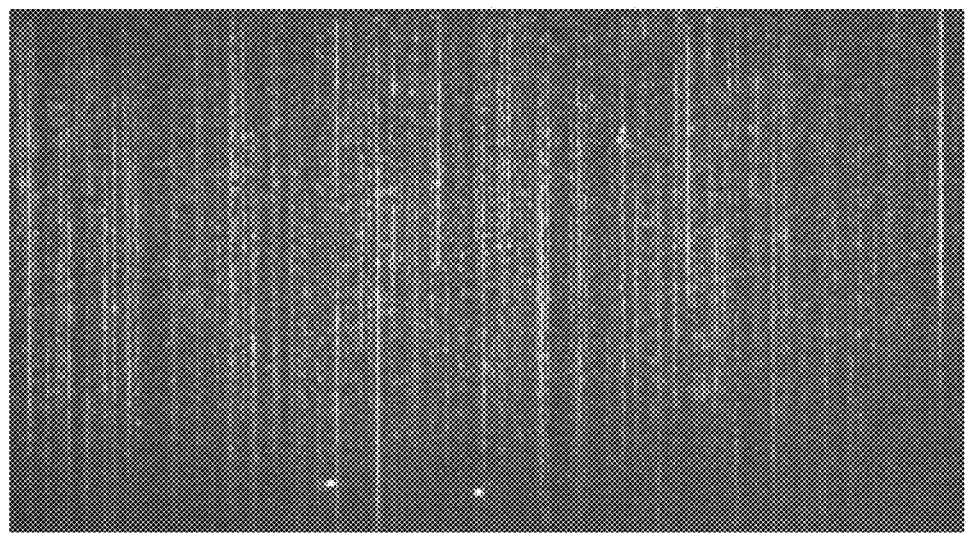
FIG. 11 is an RRS image of single-walled carbon nanotubes according to a one embodiment.

In another embodiment, the carbon nanotube sample 100 directly grows on the substrate 203. The substrate 203 is made of quartz. FIG. 11 is RRS image of single-walled carbon nanotubes directly grows on the substrate 203.

Figure 12:
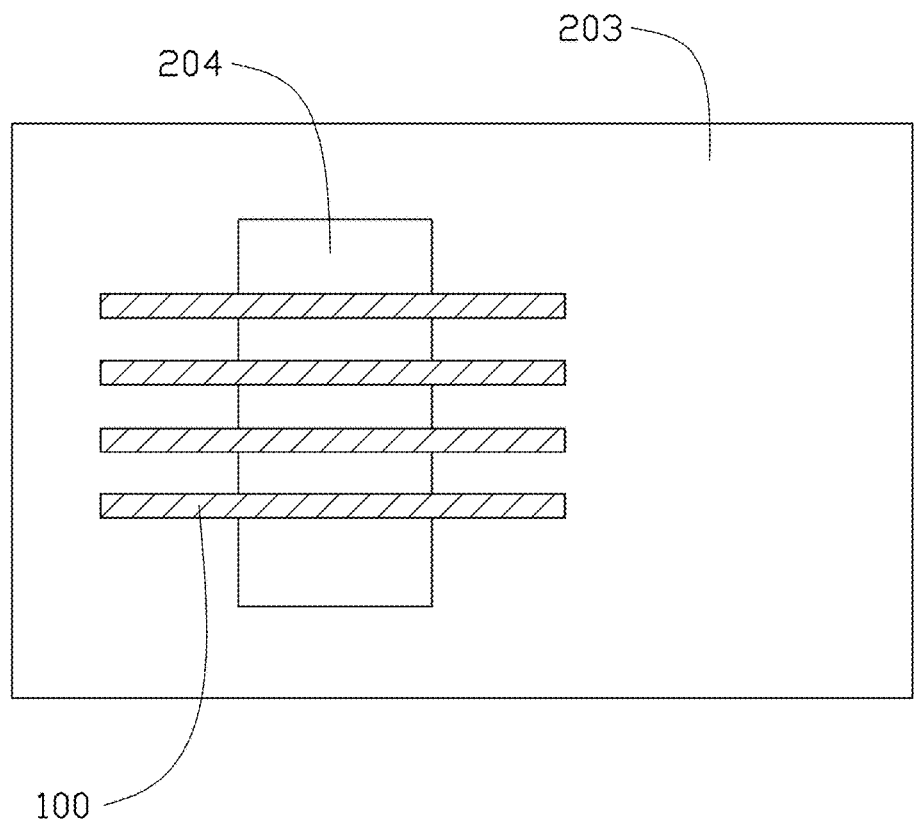
FIG. 12 shows carbon nanotubes located on a substrate with a groove according to one embodiment.

Referring to FIG. 12, in one embodiment, a groove 204 is defined on the substrate 203. The carbon nanotube sample 100 is suspended over the groove 204. Such setting can decrease the effect to observation by scattering of the substrate 203.

Figure 13:
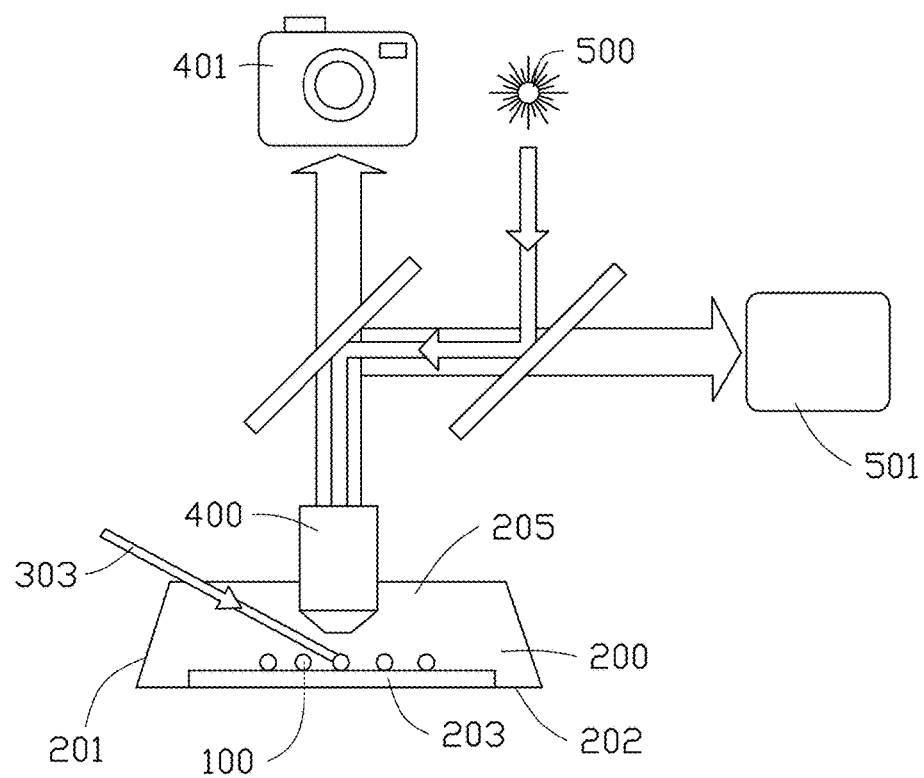
FIG. 13 shows a schematic view of a measurement device system for assigning carbon nanotubes under optical microscopy and spectra collecting according to another embodiment.

Referring to FIG. 13, in one embodiment, the incident light beam 300 is induced into the liquid 205 by an optical fiber 303.

Compared with the prior art, the measurement method of chirality of the carbon nanotube immersing the carbon nanotube sample 100 in the liquid 205 to enhance resonance Rayleigh scattering via interface dipole enhancement effect presents at the interface between the carbon nanotube example 100 and the liquid 205. Consequently colorful SWCNTs on substrates can be directly imaged under an optical microscope by wide field supercontinuum laser illumination, which facilitates high throughput chirality assignment of individual SWCNTs.

Finally, it is to be understood that the above-described embodiments are intended to illustrate rather than limit the disclosure. Variations may be made to the embodiments without departing from the spirit of the disclosure as claimed. The above-described embodiments illustrate the scope of the disclosure but do not restrict the scope of the disclosure.

It is also to be understood that the above description and the claims drawn to a method may include some indication in reference to certain steps. However, the indication used is only to be viewed for identification purposes and not as a suggestion as to an order for the steps.

What is claimed is:

1. A method for assigning chiralities of carbon nanotubes comprising steps of:
   S10, providing a carbon nanotube sample, an optical microscope with a liquid immersion objective, a liquid and a prism, wherein the prism comprises a side surface and a top surface, an angle between the side surface and the top surface is less than 90 degrees, and the carbon nanotube sample is located on the top surface;
   S20, immersing the carbon nanotube sample in the liquid;
   S30, illuminating the carbon nanotube sample by an incident beam through the side surface to generate resonance Rayleigh scattering, resonance Rayleigh scattering is generated when the carbon nanotube sample is illuminated by the incident beam; wherein the incident beam is a white light with a continuous spectrum;
   S40, immersing the liquid immersion objective into the liquid to get a resonance Rayleigh scattering (RRS) image of the carbon nanotube sample; and
   S50, measuring resonance Rayleigh scattering spectra of the carbon nanotube sample to obtain a chirality of the carbon nanotube sample.

2. The method as claimed in claim 1, wherein in step S10, the carbon nanotube sample comprises carbon nanotubes horizontally aligned on a substrate, and the carbon nanotubes are parallel to each other.

3. The method as claimed in claim 2, wherein the substrate is a Si substrate coated with a $SiO_2$ layer, the substrate has a thickness of 1000 nanometers, and the $SiO_2$ layer has a thickness of 100 nanometers.

4. The method as claimed in claim 3, wherein the liquid is oil, and the liquid immersion objective is oil liquid immersion objective.

5. The method as claimed in claim 4, wherein in step S20, the oil is disposed on the carbon nanotube sample, and the carbon nanotube sample is covered by the oil.

6. The method as claimed in claim 5, wherein in step S30, and the incident beam is orthogonal to the side surface and illuminates to the carbon nanotube sample through the side surface and the top surface.

7. The method as claimed in claim 1, wherein the incident beam is filtered and focused before reaching the carbon nanotube sample.

8. The method as claimed in claim 1, wherein in step S40, a camera is connected to the optical microscope to record the RRS image of the carbon nanotube sample.

9. The method as claimed in claim 1, wherein in step S50, spectral information of the carbon nanotube samples obtained by a spectrometer.

10. The method as claimed in claim 9, wherein the spectral information is Rayleigh scattering spectra, Raman scattering spectra, or fluorescence spectral information.

11. The method as claimed in claim 9, wherein in step S50, the Rayleigh scattering spectra and the Raman scattering spectra of the carbon nanotube sample are measured to obtain chiral indices of the carbon nanotube sample.

12. The method as claimed in claim 11, wherein the Raman scattering spectra of the carbon nanotube sample is obtained on the basis of the Rayleigh scattering spectra of the carbon nanotube sample comprises steps of:
    S51, measuring resonance Rayleigh scattering spectra of the carbon nanotube sample;
    S52, selecting excitation wavelength needed to produce Raman scattering by Rayleigh scattering spectra of the carbon nanotube sample; and
    S53, obtaining the Raman scattering of the carbon nanotube sample.

13. The method as claimed in claim 12, wherein the Raman spectra of the carbon nanotube sample is excited by a light source.

14. The method as claimed in claim 1, wherein the carbon nanotube sample is a single-walled carbon nanotube.

15. The method as claimed in claim 1, wherein the angle between the side surface and the top surface is in a range from 45 degrees to 90 degrees.

16. The method as claimed in claim 1, wherein the angle between the side surface and the top surface is 75 degrees.

* * * * *